(12) United States Patent
Giebeler et al.

(10) Patent No.: US 9,279,730 B2
(45) Date of Patent: Mar. 8, 2016

(54) DEVICE HAVING A MEMBRANE STRUCTURE FOR DETECTING THERMAL RADIATION, AND METHOD FOR PRODUCTION THEREOF

(75) Inventors: Carsten Giebeler, Edinburgh (GB); Matthias Schreiter, Munich (DE); Christian Paulus, Weilheim (DE)

(73) Assignee: Pyreos, Ltd., Edinburgh (GB)

( * ) Notice: Subject to any disclaimer, the term of this patent is extended or adjusted under 35 U.S.C. 154(b) by 1433 days.

(21) Appl. No.: 12/601,556

(22) PCT Filed: May 28, 2008

(86) PCT No.: PCT/EP2008/004246
§ 371 (c)(1),
(2), (4) Date: Sep. 27, 2010

(87) PCT Pub. No.: WO2008/145353
PCT Pub. Date: Dec. 4, 2008

(65) Prior Publication Data
US 2011/0006211 A1 Jan. 13, 2011

(30) Foreign Application Priority Data
May 29, 2007 (DE) .......................... 10 2007 024 902

(51) Int. Cl.
*G01J 5/02* (2006.01)
*G01J 5/34* (2006.01)
(Continued)

(52) U.S. Cl.
CPC .. *G01J 5/34* (2013.01); *G01J 5/023* (2013.01); *G01J 5/0205* (2013.01); *G01J 5/0225* (2013.01);
(Continued)

(58) Field of Classification Search
CPC ............ G01J 5/00; G01J 5/34; G01J 1/0204; G01J 5/0205; G01J 5/0215; G01J 5/0881; G01J 5/0225; G01J 1/0271; G01J 5/04; G01J 5/041; G01J 5/046; G01J 5/048; G01J 1/0407; G01J 5/0875; G01J 1/4228; G01J 2001/4228; G01J 5/023

USPC ............................................ 250/338.1, 338.3
See application file for complete search history.

(56) References Cited

U.S. PATENT DOCUMENTS 4,044,251 A * 8/1977 Taylor et al. .................. 250/342
5,895,233 A 4/1999 Higashi et al.
(Continued)

FOREIGN PATENT DOCUMENTS

DE 195 25 071 A1 1/1997
DE 100 04 216 A1 8/2001
(Continued)

OTHER PUBLICATIONS

German and English machine translations of Japanese Office Action for corresponding JP Application No. 2010-509728 dated Oct. 28, 2013.
(Continued)

*Primary Examiner* — David Porta
*Assistant Examiner* — Carolyn Igyarto
(74) *Attorney, Agent, or Firm* — Edell, Shapiro & Finnan, LLC

(57) ABSTRACT

In a device for detecting thermal radiation, at least one membrane is provided on which at least one thermal detector element is mounted for the conversion of the thermal radiation into an electric signal and at least one circuit support for carrying the membrane and for carrying at least one readout circuit for reading out the electrical signal, the detector element and the readout circuit being connected together electrically by an electric contact which passes through the membrane. In addition, a method of producing the device with the following method steps is provided: a) provision of the membrane with the detector element and of at least one electrical through-connection and provision of the circuit support and b) bringing together the membrane and the circuit support in such a manner that the detector element and the readout circuit are connected together electrically by an electrical contact passing through the membrane. Production activity is preferably carried out at wafer level: functionalized silicon substrates are stacked upon one another, firmly bonded to one another and then divided into individual elements. Preferably, the detector elements comprise of pyro-electrical detector elements. The device finds application in motion detectors, presence detectors and in thermal imaging cameras.

20 Claims, 1 Drawing Sheet

(51) Int. Cl.
*G01J 5/14* (2006.01)
*G01J 5/22* (2006.01)
*G01J 5/04* (2006.01)
G01N 21/01 (2006.01)
H01L 27/146 (2006.01)
H01L 41/09 (2006.01)
G01J 5/00 (2006.01)
G01J 5/20 (2006.01)

(52) U.S. Cl.
CPC .. *G01J 5/04* (2013.01); *G01J 5/041* (2013.01); *G01J 5/045* (2013.01); *G01J 5/14* (2013.01); *G01J 5/22* (2013.01); *G01J 5/00* (2013.01); G01J 2005/0077 (2013.01); G01J 2005/204 (2013.01); G01N 2021/0106 (2013.01); H01L 27/14683 (2013.01); H01L 41/0973 (2013.01); Y10T 156/10 (2015.01)

(56) References Cited

U.S. PATENT DOCUMENTS

| | | | |
|---|---|---|---|
| 6,339,187 | B1 | 1/2002 | Inoue |
| 6,551,853 | B2 | 4/2003 | Toyoda |
| 6,655,834 | B1 | 12/2003 | Frey et al. |
| 6,750,452 | B1* | 6/2004 | Morita ............... 250/338.1 |
| 7,205,545 | B2* | 4/2007 | Ouvrier-Buffet et al. ............... 250/339.05 |
| 2004/0052940 | A1* | 3/2004 | Griffin ............... 427/226 |
| 2004/0256559 | A1* | 12/2004 | Ryu et al. ............... 250/338.3 |
| 2005/0274892 | A1 | 12/2005 | Oda |
| 2006/0208189 | A1 | 9/2006 | Vilain |
| 2007/0108388 | A1* | 5/2007 | Lane et al. ............... 250/353 |

FOREIGN PATENT DOCUMENTS

| | | |
|---|---|---|
| EP | 1 184 335 B1 | 2/2006 |
| JP | 1-308927 A | 12/1989 |
| JP | 5-5652 A | 1/1993 |
| JP | 07128140 A | 5/1995 |
| JP | 09506712 A | 6/1997 |
| JP | 2000298060 A | 10/2000 |
| JP | 2003100919 A | 4/2003 |
| JP | 2003-166876 A | 6/2003 |
| JP | 2004093535 A | 3/2004 |
| WO | WO 02/43154 A1 | 5/2002 |
| WO | WO 2007/000172 A1 | 1/2007 |
| WO | WO 2007/054111 A1 | 5/2007 |

OTHER PUBLICATIONS

German and English machine translations of Japanese Office Action for corresponding JP Application No. 2010-509728 dated Aug. 4, 2014.

Japanese Office Action for corresponding JP Application No. 2010-509728 dated Oct. 28, 2013.

Japanese Office Action for corresponding JP Application No. 2010-509728 dated Aug. 4, 2014.

* cited by examiner

DEVICE HAVING A MEMBRANE STRUCTURE FOR DETECTING THERMAL RADIATION, AND METHOD FOR PRODUCTION THEREOF

BACKGROUND OF THE INVENTION

1. Field of the Invention

The invention relates to a device for detecting thermal radiation of the type having at least one thermal detector element to convert the thermal radiation into an electrical signal, and to a method of production of such a device.

2. Description of the Prior Art

A device for detecting thermal radiation is known from, for example, DE 100 04 216 A 1. This device is described as a pyro-detector. The detector element is a pyro-electrical detector element. It has a layer construction comprising two electrode layers with a pyro-electrical layer having pyro-electrical sensitive material arranged between the electrode layers. This material is Lead Zirconate Titanate (PZT). The electrodes comprise, for example, platinum or of a heat-absorbing chromium/nickel alloy.

The thermal detector element is connected to a detector support made of silicon (silicon-wafer). To provide electrical and thermal insulation between the detector element and the detector support an insulating layer is arranged between the detector element and the detector support. The insulating layer has an evacuated cavity which extends over an area of the detector element, a support layer for the cavity and a cover over the support layer and the cavity. The support layer comprises poly-silicon. The cover is made of a boron-phosphorus-Silicate glass (BPSG). To read out, process and/or further transmit the electrical signals produced by the detector element a readout circuit is integrated in the detector support. The readout circuit is produced by the application of CMOS (Complementary Metal Oxide Semiconductors) technology.

A comparable device for detecting thermal radiation is known from DE 195 25 071 A1. The thermal detector element is also a pyro-electrical detector element as described above. The detector element is arranged on a multilayer detector support. The detector element is applied to a silicon layer of the detector support at one of its electrode layers. The silicon layer is located on an electrically insulating membrane of the detector support. The membrane is formed, for example, as a triple layer—namely $Si_3N_4/SiO_2/Si_3N_4$. Once again, the membrane is applied to a silicon substrate of the detector substrate. The silicon substrate has a radiation window (detection window) with an area which for all practical purposes corresponds with an area of the pyro-electrical detector element. The radiation window is an aperture in the silicon substrate. Thereby, the support material (silicon) of the substrate is removed down to the membrane. The thermal radiation passes through the radiation window to the detector element where it produces an electrical signal which can be evaluated. In that respect the membrane distinguishes itself by providing a suitable means of transmission of the thermal radiation. In the silicon layer displaced laterally relative to the detector element a readout circuit for the electrical signal is integrated. The detector support also functions as a circuit support for the readout circuit.

In the case of the known detectors, a number of detector elements may be provided (detector element array). In that situation the electrical signal from each of the detector elements is to be read out separately. Normally, electrical contact with the electrode layers of each of the detector elements is effected by bonding wires. However, this means that considerable space is required for the wiring of the detector elements which results in a limited, relatively low packing density of the detector elements (number of detector elements per unit area of the detector support).

SUMMARY

An object of the invention is to provide a compact device for detecting thermal radiation which, in comparison with prior art, has a lower space requirement.

This object is achieved in accordance with the invention by a device for detecting thermal radiation having at least one membrane upon which is arranged at least one thermal detector element for converting thermal radiation into an electrical signal and at least one circuit support to carry the membrane and to carry at least one readout circuit to read out the electrical signal such that the detector element and the readout circuit are electrically connected together through the membrane.

This object also is achieved by a method in accordance with the invention with the following method steps for producing the device:

a) provision of the membrane with the detector element and at least one electrical through-connection and provision of the circuit support, and b) assembly of the membrane and the readout circuit support in such a manner that the detector element and the readout circuit are connected together by an electrical contact which passes through the membrane.

The membrane that functions as the detector support is composed of one membrane layer or multiple membrane layers. In this context, a number of inorganic or organic materials may be used. For example, the membrane layer may be made of silicon dioxide ($SiO_2$) or silicon nitride ($SiN_4$). Moreover, a compound structure of several of the mentioned layers is conceivable. The special advantage of layers of these materials lies in their electrical and thermal-insulation properties. These materials function as electrical and thermal insulators.

According to the invention a compact, space-saving multilayer structure comprising the membrane and the circuit carrier can be realised. The evaluation circuit can be directly integrated into the circuit support by, for example, CMOS-technology. It is also conceivable that the circuit support provides only one wire connecting with the detector element. This wire electrically connects the detector element with an internal ASIC (Applied Specific Integrated Circuit) arranged in the circuit support or with an external ASIC. The external ASIC can be bonded. It is advantageous if contact with the external ASIC is made by means of "Flip-Chip" technology (see below).

The thermal radiation to be detected has a wave length of more than 1 μm. Preferably, the wavelength is selected from the range between 5 and 15 μm. The thermal detector element is based on, for example, the Seebeck Effect. Preferably, the thermal detector element is a pyro-electrical detector element. As described initially, the pyro-electrical detector element comprises a pyro-electrical layer with a pyro-electrically sensitive material with electrode materials applied to either side. The pyro-electrically-sensitive material is, for example, a ceramic such as Lithium Niobate ($LiNbO_3$) or Lead Zirconate Titanate. A conceivable alternative is a ferroelectrical polymer such as Polyvinylidene Fluoride (PVDF). The electrode materials for the electrode layers can be, for example, platinum or a platinum alloy. A chrome-nickel electrode is also conceivable as is an electrode of an electrically-conductive oxide. Typically, the detector element has a rectangular area with an edge length of 25 μm to 200 μm.

In accordance with a particular embodiment the circuit support and the membrane are so arranged with respect to one another that there is at least one cavity between the membrane and the circuit support which is bounded by the membrane and the circuit support, this being located on the circuit side. The cavity thermally decouples the circuit support and the membrane from one another.

In a particular embodiment at least one cover is provided to shield the detector element. The circuit support, the membrane and the cover are arranged in a stack with the membrane located between the circuit support and the cover. The cover protects the detector element from harmful environmental influences. A typical environmental influence could be, for example, dust, moisture, a corrosive chemical which could attack a component of the detector element or adversely affect the function of the detector element.

In accordance with a further embodiment the membrane and the cover are so arranged with respect to one another that there is at least one cavity between the membrane and the cover, this being located on the cover side. The cavity on the cover side serves to thermally decouple the membrane or the detector element on the membrane and the cover from one another.

In order to improve the degree of thermal decoupling the cavities on the circuit side and/or cover side may be evacuated or capable of being evacuated. In that context the cavities may be evacuated independently of one another. Preferably the cavity on the circuit side and the cavity on the cover side are connected together through an opening in the membrane. The opening is, for example, a slit in the membrane. Then evacuation of one cavity then results in automatic evacuation of the other cavity.

Independent of the effect which is used to detect the thermal radiation, it is necessary in every instance for the thermal radiation to be absorbed by a thermally-sensitive material forming the detector element which releases the relevant effect. The absorption is effected directly by the thermally sensitive material. However, it is also conceivable that the thermal radiation is absorbed by an electrode or electrode layer of the detector element. Furthermore, it is also possible that the thermal radiation is absorbed by an absorption object immediately adjacent to the detector element after which a quantity of heat picked up in this way is transferred by convection or conduction to the thermally sensitive material. The absorption object acts as an energy transmitter. For example, the absorption object is applied directly to the detector element in the form of a coating.

Preferably, the device for detecting thermal radiation is designed so that the thermal radiation impinges directly on the detector element. With that in mind, in a particular embodiment the membrane, the circuit support and/or the cover have at least one radiation window with a particular transmission performance allowing the thermal radiation to irradiate the detector element. The radiation window is integrated in the cover, in the detector support and/or in the circuit support. The detector element and the radiation window are arranged with respect to one another so that the irradiation of the detector element is effected by a front face of the detector element turned away from the detector carrier (front face radiation) and/or from a rear face of the detector element turned towards the detector element (rear face radiation). The radiation window has a particular transmission capacity in the direction of the detection element. The transmission rate is as high as possible and, for example, amounts to at least 50% and in particular to between 70% and almost 95%.

Any preferred material may be used for the circuit support or the cover. Semiconducting materials, for example, elementary germanium or different semiconducting compounds are particularly suitable because of the possibility of the integration of electrical circuits or components. In accordance with a particular embodiment the circuit support and/or the cover comprises silicon. In each case a silicon substrate is used as a cover and/or as a circuit support. CMOS-technology can be employed to integrate chosen structures and functionalities into the substrate. Since silicon has a low absorption coefficient with respect to the thermal radiation the radiation window can, moreover, be very easily integrated in a silicon substrate: the silicon-substrate itself forms the radiation window. By means of a suitable arrangement of the corresponding functionalities in the silicon substrate it is possible for the thermal radiation to impinge upon the detector element in an unhindered manner, i.e. free from shadow.

The transmission performance does not depend solely upon the absorption coefficient of the material of which the radiation window is made. Another decisive factor is the thickness of the radiation window. It is advantageous if the radiation window forms a thinned area of the detector support or circuit support. In a particular embodiment, the detector element is arranged to be opposite an aperture in the cover. This aperture in the cover is an area of the cover which has a relatively low thickness. In this area the cover thickness is particularly thin, as a result of, for example, the removal of material. The aperture in the cover forms the radiation window which is integrated in the cover and through which the thermal radiation impinges upon the detector element. Preferably the detector element is distanced somewhat from the aperture in the cover. The aperture in the cover is a constituent part of the cavity between the membrane and the cover and located on the cover side.

In a particular embodiment the membrane and the circuit support and/or the membrane and the cover and/or the through-connection and the circuit support and/or the through-connection and the cover are firmly joined together by a permanent material bond and in particular, a hermetically-sealed permanent material bond. To achieve firm bonding a permanent material bond is manufactured. Firm bonding between the membrane and the circuit support is achieved by manufacturing a permanent material bond between the through-going electrical contact of the membrane and the circuit support. Firm bonding between the membrane and the cover is achieved by manufacturing a permanent material bond between the membrane and the cover.

The permanent material bond between the different constituents of the device can be produced simultaneously or consecutively. The permanent material bonds are designed in such a way that cavities (cover-side located or switch-side located) capable of being evacuated are formed. Components of the device which find themselves in cavities, for example, the detector element in the cover-side located cavity are protected from the environment by the hermetic permanent material bond. No exchange of material with the surrounding environment can take place. This allows the device to be used in an aggressive environment.

Each permanent material bond can be formed of a preferred material, for example, an adhesive. It is particularly advantageous to insert an electrically-conducting connection between the electrode layers and the readout circuit at the same time that the permanent material bond is put in place. To that end the permanent material bond in a particular embodiment has an electrically-conductive material. This relates particularly to the permanent material bond between the through-going electrical contact integrated into the membrane and the circuit support or the readout circuit integrated into the circuit support. However, a permanent material bond with conductive capability can be advantageous when located between the cover and the membrane or the detector element on the membrane if wiring components for the detector elements are integrated into the cover.

The so-called 'Flip-Chip' technology is predestined for the manufacture of the permanent material bond. By this is understood an assembly method associated with construction and connection technology (AVT), which above all else in the field of electronics has proved itself effective for producing contacts with semiconductor microchips or integrated circuits in non-housed form. Using Flip-Chip technology a chip without any connecting wires is mounted directly on the substrate with an active contact side facing downwards (circuit support). Permanent fixing is effected by means of so-called 'bumps' made of electrically-conductive material. This results in very short lead lengths. This is exploited by the present invention: it results in a compact device built. Moreover, as a consequence of the very short lead lengths undesirable scatter inductivity and capacitance effects which interfere with the electrical signals to be read out are reduced to a minimum. This influence operates in a particularly advantageous manner when there are a relatively small number of detector elements to be connected up. With the help of the Flip-Chip technology, moreover, a number of electrical connections can be made simultaneously which results in enormous savings in cost and time.

Different techniques can be employed to implement the 'Flip-Chip' technology and, as a consequence, the manufacture of the permanent material bond. In a particular embodiment one of the group comprising adhesion, soldering and/or bonding methods can be selected for use. In that context adhesive bonding or eutectic bonding are both conceivable. In the case of soldering, solder bumps (soldering spheres) are applied to one or both of the support features or components of the device to be joined together. The named methods are preferred in comparison with adhesion since when an adhesive is used out-gassing of organic substances (solvents, adhesive material, . . . ) can occur. Particularly in relation to the evacuation of the cavities this is a factor to be borne in mind. Nevertheless, it can be necessary or advantageous to have recourse to the use of an adhesive.

When using an adhesive a number of different options are available: adhesion can be effected by using an adhesive which is not electrically conducting. In that situation, bumps are applied to the contact areas of the appropriate support features. The bumps comprise, for example, aluminium or gold. After that a layer of the adhesive is applied and the appropriate element arranged on the adhesive layer. As it dries, the adhesive shrinks and forms the electrical contacts.

Equally, an isotropic conductive adhesive can be used. Conductive adhesive material is applied to the contact surfaces of a support feature. Then the object with its contact areas is placed on the points provided with adhesive. The adhesive can be hardened thermally or by using UV-radiation thereby causing the electrically-conducting material bond to be made.

Alternatively, an anisotropic conductive adhesive can be used. An anisotropic conductive adhesive is a bonding material formed of an electrically non-conductive adhesive with a low content of electrically-conductive particles. The anisotropic conductive adhesive is placed upon the contact areas of the support feature (circuit support, membrane). As a result of the low content of electrically-conductive particles they are not in contact with one another after the adhesive has been applied. No electrically-conductive contact is made. When the object is placed in position the non-electrically-conductive adhesive is compressed until the particles between the contact areas of the support feature and the contact areas of the applied object are forced together thereby producing an electrically-conductive join between the contact areas.

To provide the membrane the following method steps in particular are to be taken: d) providing of a sacrificial support element using sacrificial material, c) the arrangement of a membrane on a section of the surface of the sacrificial support element and bringing together the membrane and a membrane support element to carry the membrane and e) removal of the sacrificial material so that the membrane is at least partially released. Preferably, the sacrificial support element comprises silicon. The membrane support element serves, for example, as the temporary support for the membrane. However, the membrane support element can later be used as the cover for the detector element. The arrangement of the membrane on the sacrificial support and the bringing together of the membrane and the membrane support feature can take place simultaneously or consecutively. In this respect, the removal of the material means, for example, eroding away the reverse face of the silicon down to the membrane. Furthermore, the membrane remains on the membrane support with the through-connection which is connected to the circuit support.

Creating the through-connection can be achieved using a variety of steps method steps. In accordance with a particular embodiment the following further method steps are carried out before the arrangement of the membrane on the sacrificial support or after the arrangement of the membrane on the sacrificial support: f) drilling a hole in the membrane and g) filling the hole with an electrically-conductive material, so that the electrical contact is made.

In accordance with a particular embodiment of the method the cavity on the cover side and/or the cavity on the circuit side are evacuated while and/or after the firm connection is being made. For example, the manufacture of the permanent material bond between the components of the stack takes place under vacuum. Each cavity is evacuated with the formation of the permanent material bond. It is also conceivable that the cavities are formed first and evacuated later. It is to be remembered here that the cavities may be evacuated consecutively or simultaneously. In the case of simultaneous evacuation the cavities may be connected in an isobaric manner. This means that the pressure in the two cavities in the stack is the same and the cavities are connected by, for example, a hole in the membrane.

The device can have a single detector element. With regard to the device being used as a presence detector or, in particular, as a heat-sensitive camera it is however, desirable and even necessary that several detector elements are provided. In a particular embodiment, therefore, at least one array with several detector elements is provided. This means one detector element represents a pixel in the array. The detector array is characterised by, for example, a columnar and/or cellular arrangement of the detector elements. In the case of a cellular or a columnar arrangement the detector elements are distributed in one dimension in a particular direction. In the case of a columnar and a cellular arrangement the distribution is of a two-dimensional nature. The detector array comprises, for example, 240×320 individual elements. This corresponds to the relatively low resolution standard QVGA. It is also conceivable to choose an area-type distribution of the detector elements. A radiation window can be provided for each detector element. It is advantageous, however, that the device has a single radiation window for several or all of the detector elements. This allows the manufacture of the device to be simplified.

In accordance with a further embodiment the device has a casing. From the firm attachment of the membrane and the circuit support and from the firm attachment of the membrane and the cover there results a stack, around which a casing is arranged. This casing protects the stack and its component parts against harmful environmental influences, for example, moisture—and also against mechanical damage. The one point to be ensured here is that the radiation falling on the detector element is not adversely affected by the casing. To that end, a radiation window permitting a high rate of transmission of thermal radiation is integrated into the casing.

The casing may comprise a housing made of any chosen material. Preferably, the housing is a casting compound. To provide the casing one of the group of injection moulding methods or moulding methods may be used. These methods are particularly advantageous on cost grounds. The method involves applying non or partially cross-linked synthetic material to the stack. Then the synthetic material is thermally induced or hardened by exposure to UV light. To integrate the radiation window a mask is used, for example, which is removed once the synthetic material has been put in place or after that material has been hardened. This is achieved by using, for example, transfer moulds fitted with a spring-loaded insert. It is also conceivable to employ a radiation window fabricated from a material which has a higher transmission rate for thermal radiation which remains in the casing after the synthetic material has been put in place and hardened.

The described method may be used to manufacture a single device for detecting thermal radiation. It is advantageous, however, if several devices are manufactured at the same time in parallel. In a particular embodiment, therefore, a number of devices for the detection of thermal radiation are manufactured at wafer-level. When manufacture is complete the devices or the stacks are separated. Wafers are used for the circuit supports and possibly the covers and, in particular, silicon wafers each of which is provided with a number of relevant components and functionalities which are brought together as described above. The stacks are separated from one another, preferably before the application of the casing. The separation or division takes place by, for example, sawing, erosion, or similar methods. When separation is complete a casing is applied to each of the stacks of the devices.

In accordance with a further aspect of the invention the device is used as a motion detector, a presence detector and/or as a thermal image camera. For a movement reporter a device with a single detector element can be adequate. For a presence reporter the device can be fitted with several detector elements. For the thermal imaging camera, the device needs a large number of detector elements, for example, 240×320 detector elements (to qualify for the QVGZ standard). This can be achieved by using the simple and space-saving wiring technique for the detector elements.

Summarising, the following advantages of the invention may be identified:

The device for detecting thermal radiation is compact.

Because of the sandwich construction a number of detector elements can be connected in a space-saving manner.

The electrical leads between the electrodes of a detector element and the assigned readout circuit or readout element are short. Inductive and capacitance-effects which lead to interference which affect the detection capability of the detector elements are clearly reduced by comparison with bonded wires.

By virtue of the way in which contacts are made it is possible to introduce a high degree of parallelisation into the manufacturing operation.

Because of the hermetic permanent material bond, access is easy to the cavities which are capable of being evacuated and lead to improved sensitivity of the device and to protection of the detector elements.

BRIEF DESCRIPTION OF THE DRAWINGS

By making reference to a number of embodiments and the associated figures there follows a presentation of a device for detecting thermal radiation. The figures are of a schematic nature and are not to scale.

DESCRIPTION OF THE PREFERRED EMBODIMENTS

Figure 1:
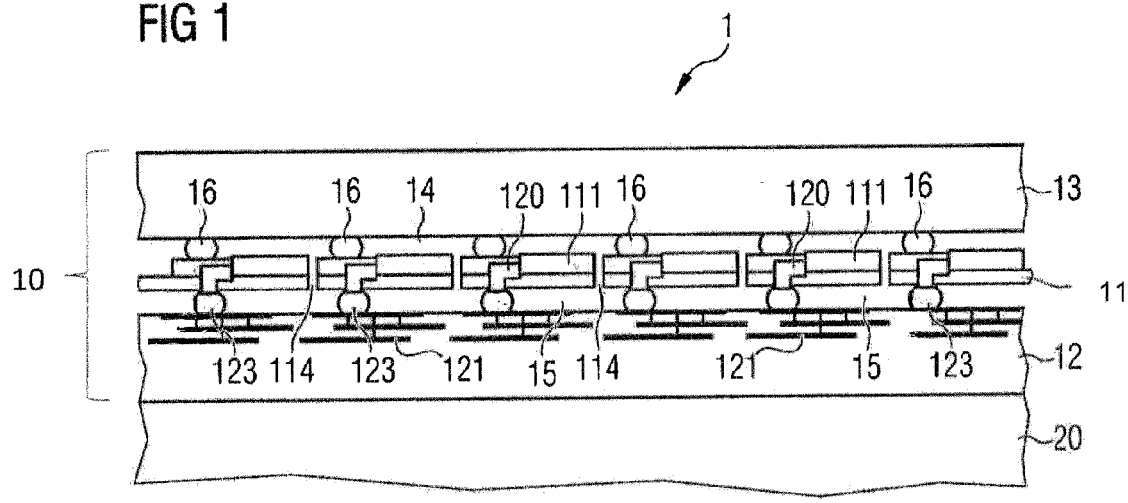
FIG. 1 shows a device for detecting thermal radiation in cross-section.
Figure 2:
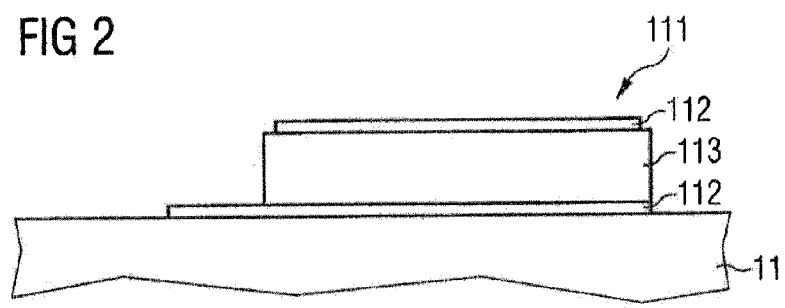
FIG. 2 shows a detector element on a detector support in cross-section.

The device 1 for the detection of thermal radiation has a stack 10 with a membrane 11 with a detector array of detector elements 111 for the conversion of thermal radiation into electric signals, an circuit support 12 with 5 a readout circuit 121 for reading-out the electric signals and at least one cover 13 to cover the detector elements, wherein the membrane and the cover are so arranged with respect to one another that between the detector elements of the detector support and the cover there is on the cover side a cavity 14 in the stack bounded by the detector support and the cover while the circuit 10 support and the are so arranged with respect to one another that between the detector support and the circuit support there is at least one cavity 15 on the circuit side bounded by the circuit support and the detector support and that the cavities are evacuated. The cavities are connected together by slits 114 in the membrane.

The detector elements are pyro-electrical detector elements of a thin-layer construction with two electrode layers 112 and a pyro-electrical layer 113 arranged between the electrode layers. The pyro-electrical layer is a layer of PZT about 1 μm thick of a pyro-electrically-sensitive nature. The electrode layers are made of platinum and a chromenickel alloy about 20 nm thick.

The membrane is a triple layer of $Si_3N_4/SiO_2/Si_3N_4$. A readout circuit is integrated into the circuit support for the detector elements.

The circuit support and the cover form a silicon substrate. The detector elements are arranged within the first stack cavity to be opposite a non-illustrated aperture in the cover. In the area of the aperture is arranged a common radiation window (also not illustrated) through which the radiation impinges upon the detector elements. The radiation passes through from the front side.

The membrane, the cover, the detector support and the circuit support are all firmly bonded together by a hermetic permanent material bond 16. In accordance with a first embodiment the permanent material bond comprises a solder material. The supports (silicon substrates) are soldered together. Alternatively, the permanent material bond is produced by bonding.

Provision is made for an electrical connection 123 to the detector elements to be made between the circuit support and the membrane. The electrical signals are read out from the detector elements by means of the wiring or the readout circuit. The permanent material bond between the cover and the membrane also comprises electrically-conductive material. Note that in each case here an element of electrical insulation (also not illustrated) is provided.

To provide the membrane the following steps are taken: the preparation of a sacrificial support made of silicon, arrangement of a membrane with a through-connection to a section of the surface of the sacrificial support and removal of the sacrificial material so that the membrane is at least partially released. To remove silicon, it is eroded away from the back as far as the membrane. This leaves the membrane with the through-connection which is then connected to the circuit support.

The through-connection can be produced by a chosen series of method steps. In accordance with a particular embodiment before the arrangement of the membrane on the sacrificial support or after the arrangement of the membrane on the sacrificial support the following method steps are taken: f) a hole is drilled in the membrane and g) the hole is filled with an electrically-conductive material so that the electrical through-connection 120 is made effective.

During the manufacture of the permanent material bonds vacuum is applied so that an under-pressure develops in the cavities being created. The cavities in the stack are evacuated while they are being formed. Alternatively, the cavities in the stack are evacuated after the permanent material bonds have been produced.

Once the stack has been produced it is provided with a casing 20. A non-cross-linked synthetic material is applied to the stack by a spray-casting technique and subsequently cross-linked. Alternatively, a moulding technique can be used. In that context care must be taken to ensure that the radiation window in the cover remains free, i.e. that window is not covered up.

To manufacture the device the membrane with the detector array, the circuit support with the readout circuit and the cover are provided and firmly connected together as described above. The next stage of manufacture is carried out at wafer level. Silicon wafers are provided with a number of appropriate functionalities (readout circuits and possibly cover apertures). The circuit support with the membrane and the cover are prepared at wafer-level. These functionalised silicon wafers are firmly connected together as described above. A wafer stack containing a number of individual stacks is produced. After the connection activity has been concluded the individual stacks are isolated by sawing through the wafer stack and each of them then provided with a casing.

The device finds application in a motion detector or a presence detector. For application in a thermal imaging camera a plurality of stacks or of devices is provided, each device having one stack.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for detecting thermal radiation comprising:
    at least one membrane upon which at least one thermal detector element for converting the thermal radiation into an electric signal is arranged; and
    at least one circuit support upon which the at least one membrane is arranged, and which carries at least one readout circuit to read out the electric signal;
    at least one cover that shields the at least one thermal detector element;
    wherein the at least one thermal detector element and the at least one readout circuit are electrically connected by an electric through-connection which passes through the entire at least one membrane,
    wherein the at least one circuit support, the at least one membrane and the at least one cover are arranged in a stack with the at least one membrane arranged between the at least one circuit support and the at least one cover,
    wherein the stack comprises a sandwich construction,
    wherein the at least one membrane and the at least one cover are arranged with respect to one another to provide at least one cavity on a cover side between the at least one membrane and the at least one cover,
    wherein the at least one membrane and the at least one circuit support are arranged with respect to one another to provide at least one cavity on a circuit side between the at least one membrane and the at least one circuit support,
    wherein the at least one cavity on the circuit side is evacuated,
    wherein the electric through-connection which passes through the entire at least one membrane and the at least one circuit support are firmly bonded together with a first hermetic permanent material bond, which is, in two dimensions, entirely surrounded by the at least one cavity on the circuit side to provide a wiring between the at least one thermal detector element and the at least one readout circuit,
    wherein the first hermetic permanent material bond comprises an electrically-conductive material and is arranged such that the at least one cavity on the circuit side is formed and components located in the at least one cavity on the circuit side are protected from a surrounding environment by the first hermetic permanent material bond.

2. The device according to claim 1, wherein the at least one cavity on the cover side is evacuated or capable of being evacuated.

3. The device according to claim 1, wherein the at least one cavity on the circuit-side and the at least one cavity on the cover side are connected by an opening in the at least one membrane.

4. The device according to claim 1, wherein the at least one circuit support and the at least one cover comprises silicon.

5. The device according to claim 1, wherein the at least one thermal detector element is arranged to be opposite to a cover aperture.

6. The device according to claim 1, wherein the at least one membrane and the at least one cover are firmly bonded together with a second hermetic permanent material bond.

7. The device according to claim 6, wherein the second hermetic permanent material bond comprises an electrically-conductive material.

8. The device according to claim 1, further comprising a plurality of the at least one thermal detector element forming at least one detector array.

9. The device according to claim 1, further comprising a casing.

10. The device according to claim 9, wherein the casing comprises a casting material.

11. The device according to claim 1, wherein each of the at least one thermal detector element is electrically connected with a readout circuit of the at least one readout circuit only by a single electric through-connection.

12. Method of producing a device having a membrane structure for detecting thermal radiation comprising:
    providing at least one membrane and arranging at least one thermal detector element upon the at least one membrane for converting the thermal radiation into an electrical signal, providing at least one electric through-connection, and at least one circuit support which carries at least one readout circuit to read out the electrical signal; and combining the at least one membrane and the at least one circuit support in such a manner that the at least one thermal detector element and the at least one readout circuit are electrically connected by the at least one electric through-connection that passes through the entire at least one membrane, wherein the at least one membrane and the at least one circuit support are arranged with respect to one another to provide at least one cavity on a circuit side between the at least one membrane and the at least one circuit support, and wherein the at least one electric through-connection which passes through the entire at least one membrane and the at least one circuit support are firmly bonded together with a first hermetic permanent material bond, which is, in two dimensions, entirely surrounded by the at least one cavity on the circuit side to provide a wiring between the at least one thermal detector element and the at least one readout circuit.

13. The method according to claim 12, further comprising:
providing a sacrificial support using a sacrificial material,
arranging said at least one membrane on a section of a surface of the sacrificial support and combining the at least one membrane and a membrane support, and
removing the sacrificial material such that the at least one membrane is at least partially released.

14. The method according to claim 13, further comprising:
drilling a hole in the at least one membrane, and
filling the hole with an electrically-conductive material thereby forming the at least one electric through-connection.

15. The method according to claim 12, further comprising:
firmly bonding of the at least one membrane and at least one cover by providing a second permanent material bond between the at least one membrane and the at least one cover.

16. The method according to claim 15, further comprising:
forming the first hermetic permanent material bond and the second permanent material bond from a group consisting of adhesives, solder material and bonding material.

17. The method according to claim 15, further comprising:
forming a stack by the firmly bonding of the at least one membrane and the at least one circuit support, and by the firmly bonding of the at least one membrane and the at least one cover; and
providing a casing at the stack.

18. The method according to claim 17, further comprising:
providing the casing by injection molding or molding.

19. The method according to claim 12, further comprising:
providing at least one cover that shields the at least one thermal detector element;
wherein the at least one circuit support, the at least one membrane and the at least one cover are arranged in a stack with the at least one membrane arranged between the at least one circuit support and the at least one cover,
wherein the stack comprises a sandwich construction,
wherein the at least one membrane and the at least one cover are arranged with respect to one another to provide at least one cavity on a cover side between the at least one membrane and the at least one cover,
wherein the at least one cavity on the circuit side is evacuated, and
wherein the first hermetic permanent material bond comprises an electrically-conductive material and is arranged such that the at least one cavity on the circuit side is formed and components located in the at least one cavity on the circuit side are protected from a surrounding environment by the first hermetic permanent material bond.

20. The method according to claim 19, further comprising:
evacuating the at least one cavity on the circuit side and at least one cavity on a cover side after the forming of the first permanent material bond and the second permanent material bond.

* * * * *